| United States Patent [19] | [11] Patent Number: 4,913,843 |
|---|---|
| Phillips et al. | [45] Date of Patent: Apr. 3, 1990 |

[54] PREDICTING THERMOPARTICULATION

[75] Inventors: D. Colin Phillips, Monroeville; James D. B. Smith, Wilkins Township, Allegheny County, both of Pa.

[73] Assignee: Westinghouse Electric Corp., Pittsburgh, Pa.

[21] Appl. No.: 559,019

[22] Filed: Dec. 8, 1983

Related U.S. Application Data

[60] Continuation of Ser. No. 260,863, May 6, 1981, abandoned, which is a division of Ser. No. 85,446, Oct. 16, 1979, abandoned.

[51] Int. Cl.⁴ ............................................. G01N 31/00
[52] U.S. Cl. .................................. 252/408.1; 252/962; 436/7; 116/201; 116/207; 116/216; 374/141; 374/159; 374/186; 374/161; 340/590
[58] Field of Search ................ 252/408.1, 962; 436/7; 73/339 R; 116/201, 202, 216; 374/141, 159, 186; 340/590; 310/52, 55

[56] References Cited

U.S. PATENT DOCUMENTS

| 3,281,376 | 10/1966 | Proops | 528/51 |
|---|---|---|---|
| 3,622,524 | 11/1971 | Markovtiz | 528/114 |
| 3,918,973 | 11/1975 | Mertens | 96/48 R |
| 3,957,014 | 5/1976 | Phillips et al. | 436/7 |
| 3,973,439 | 8/1976 | Smith et al. | 436/7 |
| 3,979,353 | 9/1976 | Smith et al. | 436/7 |
| 3,995,489 | 12/1976 | Smith et al. | 436/7 |
| 4,046,733 | 9/1977 | Smith et al. | 436/7 |
| 4,056,005 | 11/1977 | Smith et al. | 436/7 |
| 4,056,006 | 11/1977 | Smith et al. | 436/7 |
| 4,102,192 | 7/1978 | Smith et al. | 436/7 |
| 4,108,001 | 8/1978 | Smith et al. | 436/7 |
| 4,138,390 | 2/1979 | Emmons et al. | 428/522 |
| 4,142,416 | 2/1979 | Smith et al. | 436/7 |
| 4,149,161 | 4/1979 | Phillips et al. | 252/408.1 |
| 4,224,202 | 9/1980 | Heiberger | 260/22 CB |

*Primary Examiner*—Matthew A. Thexton
*Attorney, Agent, or Firm*—A. Mich, Jr.

[57] ABSTRACT

Whether a compound will thermoparticulate, that is, decompose to produce particles detectable by an ion chamber monitor or a condensation nuclei monitor and, if so, at what temperature, is predicted by determining the decomposition products of the compound, eliminating the compound if none of its decomposition products are greater than 25 Å, and using the temperature at which the decomposition products greater than 25 Å have a vapor pressure of 10 millimeters as an estimate of the temperature at which the compound will decompose to produce products detectable by the monitor. Also disclosed are compounds which have been found to thermoparticulate at low temperatures.

14 Claims, No Drawings

PREDICTING THERMOPARTICULATION

This application is a continuation of application Ser. No. 260,863, filed May 6, 1981, now abandoned, which was a division of application Ser. No. 085,446, filed Oct. 16, 1979, now abandoned.

BACKGROUND OF THE INVENTION

Electrical apparatus, such as motors and turbine generators, occasionally overheat due to shorts or other malfunctions. The longer the overheating continues the more damage is done to the apparatus. If the malfunction is detected immediately it may mean only a quick repair, but if the overheating continues, the entire machine may be damaged. Large rotating electrical apparatus is usually cooled with a hydrogen gas stream. The organic compounds in the apparatus are first to be affected by the overheating and may decompose to form particles which enter the gas stream. Monitors then detect particles in the gas stream and sound a warning or shut down the apparatus when too many particles are detected.

Special coatings may be applied to the apparatus which decompose and form detectable particles at lower temperatures than the usual organic compounds found in the apparatus. See U.S. Pat. Nos. 4,142,416; 4,108,001; 4,130,009; 4,102,809; 3,973,439; 4,102,193; 4,056,005; 3,973,438; 4,046,733; 4,046,512; 3,972,225; 4,056,006; 4,106,745; 3,957,014; 3,995,489; 3,797,353; 4,046,943; 3,973,438; and 3,995,417. The thermoparticulating compounds disclosed in these patents produce detectable signals at temperatures below 200° C., which is about the maximum temperature tolerable in turbine generators before serious damage is done to the generator.

Until now efforts to identify compounds which thermoparticulated at temperatures below 200° C. has proceeded by trial and error. At first it was thought that there might be a correlation between the thermoparticulating temperature and the melting point of the compound but after observations on over 500 organic compounds were made, it was discovered that there was no correlation between the melting point of a compound and its thermoparticulation temperature. Also, no correlation was discovered between the thermoparticulation temperature and the decomposition temperature of the organic compounds. And finally, there did not appear to be any correlation between the structure of the compounds and the thermoparticulation temperature.

SUMMARY OF THE INVENTION

We have discovered a method of predicting whether or not a compound will thermoparticulate and if so at what temperature. By means of the method of this invention one can tell from the properties of a compound and its decomposition products whether or not it will thermoparticulate and, if so, one can estimate the thermoparticulation temperature. Thus it is no longer necessary to test hundreds of compounds in the hopes of finding a few which all thermoparticulate. Rather, one can examine published data in chemical handbooks and thereby eliminate much unnecessary laboratory work.

Using the method of prediction of this invention we have discovered many compounds which thermoparticulate at low temperatures.

DESCRIPTION OF THE PRIOR ART

The patents listed in the Background of the Invention are the best known prior art.

DESCRIPTION OF THE INVENTION

In order to determine whether or not a compound will thermoparticulate, that is, decompose to produce particles detected by an ion chamber monitor or a condensation nuclei monitor, and if so, at what temperature it will thermoparticulate, it is first necessary to determine the probable decomposition products of the compounds, because if the decomposition products are not larger than 25Å they are not detectable by the ion chamber monitor. The decomposition products of some compounds are better known and described in the literature. If the decomposition products are not described in the literature they can be determined by identifying the activation energy of the different bonds in the compound so that one can tell which bonds will break first and, therefore, what the resulting products will be. If the degradation products are less than 25Å but are capable of hydrogen bonding with themselves, they can form products which are greater than 25Å and which will be detectable by the ion chamber monitor. Any compound which is not capable of forming at least one decomposition product greater than 25Å is eliminated from consideration.

It has been found that the temperature at which the decomposition products have a vapor pressure of 10 mm is a very good estimate of the thermoparticulation temperature of the compound. Thus, once the decomposition products larger than 25Å have been identified one can refer to published data to determine at what temperature they have a vapor pressure of 10 mm and thereby estimate the thermoparticulation temperature of the initial compound. This procedure will be further illustrated in the examples to follow.

The compounds which thermoparticulate at low temperatures which have been discovered using the method of this invention are typically incorporated in a resinous composition for application to the generator and other types of apparatus. A composition is prepared of the thermoparticulating compound in a solution of a resinous carrier. The thermoparticulating compound may be dispersed if it is insoluble in the solvent or it may be in solution if it is soluble in the solvent. Dispersions are preferred as they produce a stronger signal than do solutions. A particle size of the dispersed thermoparticulating compound of about 25 to about 1,000 microns is suitable.

An acceptable composition is a resinous carrier, about 20 to about 250 phr (parts by weight per hundred parts of resinous carrier) of thermoparticulating compound, and about 25 to about 75% (by weight based on the resinous carrier) of a solvent for the resinous carrier. If the amount of thermoparticulating compound is less than about 20 phr the quantity of particles given off during decomposition may be too low to be detected by presently existing detectors. However, the construction of more sensitive detectors would permit a lower amount of thermoparticulating compound. If the amount of thermoparticulating compound exceeds about 250 phr the composition is thick, difficult to apply, and does not bond well. The preferred amount of thermoparticulating compound, which usually gives the best results, is about 40 to about 60 phr. If the amount of solvent is less than about 25% the composition is generally too viscous to apply easily and if the amount is greater than about 75% the composition is unnecessarily dilute and the coating may be too thin to produce an adequate number of particles during decomposition, at least while the malfunction is highly localized. Best results are usually obtained with about 45 to 55% solvent. The composition also contains about 0.1 to about 3 phr of a drier for the resinous carrier when it is an epoxy resin or similar resin to promote its room temperature cure. Lead naphthenate or cobalt naphthenate is preferred although stannous octoate, zinc stearate, etc., could also be used. Resins such as polyesters may also require the presence of an organic peroxide as is known in the art. Mixtures of various resins, solvents, or driers are contemplated.

The composition may be prepared by simply mixing the ingredients but it is preferable to mix the drier, resinous carrier, and solvent first and add the thermoparticulating compound later to prevent the inclusion of the drier in the thermoparticulating compound and thereby obtain a more homogeneous dispersion of the thermoparticulating compound.

The thermoparticulating compounds of the invention may be described by ten general formulae. The first group of compounds have the general formula $M^+(R)_4 X^-$, where M is nitrogen, phosphorus, arsenic, or antimony, each R is independently selected from hydrogen, alkyl $C_{20}$, aryl, alkaryl $C_{20}$, aralkyl $C_{20}$, heterocyclic with nitrogen, oxygen or sulfur, or substituted aromatic with nitro or halide substituents, and X is chloride, bromide, iodide, carboxylic $C_{20}$, dimethyl phosphate, or hydroxide. Preferred compounds which have been found to give strong signals at low temperatures include tetrabutyl phosphonium acetate, tetrabutyl phosphonium chloride, triphenylmethyl phosphonium iodide, methyltrioctyl phosphonium dimethyl phosphate, tetrabutyl arsonium chloride, tetraphenyl arsonium iodide, tetrabutyl stibonium chloride, tetraphenyl stibonium iodide, triphenyl methyl stibonium bromide, triethylmethyl ammonium chloride, triethylmethyl ammonium iodide, and triethyl, n-propyl ammonium iodide. M is preferable nitrogen or phosphorus as those compounds are readily available. R is preferably alkyl to $C_8$ or benzyl as those compounds give stronger signals. X is preferably chlorine, iodide, or acetate as those compounds give stronger signals.

The second group of compounds has the general formula $M'(C_xH_yO_z)_n$ where M' is copper, chromium, iron, cobalt, nickel, lead, titanium, zinc, zirconium, sodium, or potassium, x is 6, 7, or 9, y is 7, 9, or 11, z is 2, 3, or 4, and n is 1 to 3. M' is preferably copper, iron, cobalt, nickel, or lead as these compounds are less thermally stable and gives stronger signals at low temperatures. X is preferably 6, y is preferably 9, z is preferably 3, and n is preferably 2 or 3, especially 3, as these compounds give stronger signals. Examples of suitable compounds include copper ethyl acetoacetate, chromium ethyl acetoacetate, iron (ferric) ethyl acetoacetate, copper diethyl malonate, zinc diethyl malonate, chromium diethyl malonate, copper formyl acetophenone, and chromium formyl acetophenone.

The third group of compounds has the general formula $M''R'_mA_n$ where M'' is tin, antimony, titanium, boron, phosphorus, or chromium, R' is R, halide, or oxygen, A is amine, amide, catechol, or pyrogallol, and m is 1 to 5. Preferably M'' is tin, boron, or chromium and A is a primary amine up to $C_4$, a primary amide up to $C_4$, or catechol as these compounds give stronger signals. Examples of suitable compounds include triphenyltin chloride-morpholine, triphenyltin chloride-n-propylamine, diphenyltin dichloride-morpholine, diphenyltin dichloride-benzyldimethylamine, boron trifluoride-monoethylamine, antimony pentafluoride-triethylamine, antimony pentachloride-pyridine, and titanium tetrachloride-morpholine.

The fourth group of compounds are amine-picric acid molecular complexes having the general formula

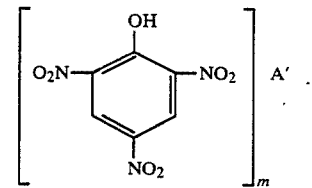

where A' is A, anthracene, naphthalene, phenanthrene, or corononene. Examples of suitable compounds include n-butylamine picrate, triethylamine picrate, m-phenylene diamine picrate, 1-methylimidazole picrate.

The fifth group of compounds are extra-coordinate siliconate salts having the general formula

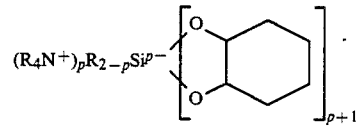

where p is 1 or 2. For these compounds R is preferably hydrogen or alkyl $C_4$ as these compounds give stronger signals. Examples of suitable compounds include benzyl dimethyl ammonium bis (0-phenylene dioxy) phenyl siliconate, triethylammonium bis (0-phenylene dioxy) phenyl siliconate, and triethanolamine bis (0-phenylene dioxy) phenyl siliconate.

The sixth group of compounds are glyoximes having the general formula

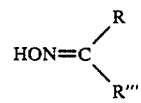

where R''' is R or

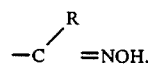

Preferably R''' is

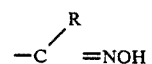

and also R is preferably hydrogen as these compounds are more readily available.

The seventh group of compounds are sulfamic acids having the general formula

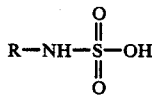

The preferred compound under this general formula is cyclohexene.

The eight group of compounds are thiosemicarbazides having the general formula

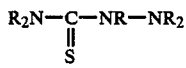

Preferably at least one of the R groups is hydrogen as this leads to hydrogen bonding in the decomposition products.

The ninth group of compounds are nitronaphthols having the general formula

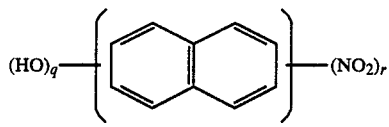

where q is 1 to 4 and r is 1 to 7. An example is 2,4-Dinitro-1-naphthol.

The tenth group of compounds are anthranols having the general formula

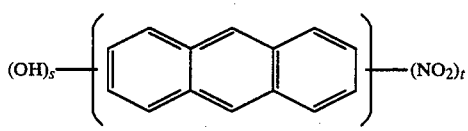

where s is 1 to 6 and t is 1 to 9.

In all of the above general formulae the same definitions of the various groups are applicable to all formulae.

The resinous carrier used in the composition performs a function of bonding the thermoparticulating compounds to the apparatus since the coating of the thermoparticulating compounds by themselves does not adhere well. The resinous carrier should be compatible with the other resins used in the apparatus and therefore it is usually advantageous to use these same resins used elsewhere. The resinous carrier is curable at 60° C. and is preferably air dryable since it cannot be easily cured in place with heat. Also, it should be stable, after curing, for several years at 60° C. The resin must be substantially unreactive with the thermoparticulating compound for otherwise suitable thermoparticulation will not occur. The thermoparticulating compound and the resin form a mixture and the thermoparticulating compound does not catalyze the cure of the resin. Epoxy resins are preferred as they are usually used elsewhere in the apparatus. Polyester resins, silicon rubber, polystyrene, etc. could also be used. The solvent for the resinous carrier depends on the particular resinous carrier used. Toluene, xylene, benzene, methylethyl ketone, ethyl alcohol, diethyl ether, acetone, cellosolve, etc. or other common solvents may be used. Toluene is preferred as it is inexpensive and dissolves most resins.

The composition is applied to portions of the electrical apparatus which are exposed to the gas stream. The coating does not function as insulation and is usually applied on top of insulation, but it can also be applied to conductors. The application may be made by brushing, spraying, dipping, grease gun, troweling, or other techniques. A suitable coating thickness (after drying) is about 1/16 to about 1/8 inch. The dispersed particles of thermoparticulating compound should not be covered with excessive resinous carrier as that may prevent the decomposition products from escaping into the gas stream. After evaporation of the solvent and room temperature cure of the resinous carrier, if necessary, the apparatus is ready to be operated. The monitor can be an ion chamber monitor, where the presence of particles lowers the current flowing across a sample of the gas stream, or a condensation nuclei monitor, where the presence of particles condenses water vapor obscuring a light beam. When thermoparticulation occurs and the monitor sounds an alarm a sample of the gas stream can be collected and analyzed. Since different thermoparticulating compounds can be used in different areas of the apparatus and their thermoparticulation products are different, analysis of the sample can pinpoint the location of the overheating.

The following examples further illustrate this invention.

EXAMPLE 1

Compositions were prepared as follows using various thermoparticulating compounds:

|  | Parts by Weight |
| --- | --- |
| Thermoparticulating compound | 100 |
| Epoxy resin, 50% solids in toluene, made from 200 pbw (parts by weight) linseed fatty acids, 200 pbw styrene, and 300 pbw diglycidyl ether of Bisphenol A, sold by Westinghouse Electric Corporation as "B-276" Varnish (See Example I of U.S. Pat. No. 2,909,497 for detailed description) | 100 |
| 6% solution in low boiling hydrocarbons of cobalt naphthenate | 1.0 |
| 24% solution in low boiling hydrocarbons of lead naphthenate | 0.25 |

The cobalt and lead naphthenate solutions were added to the epoxy resin prior to the addition of the thermoparticulating compound.

Samples were prepared by brushing the above composition onto 3 inch by 1 inch aluminum sheets 1/16 to ¼ inch thick. The samples were dried overnight at 60° C. to form coatings ¼ inch thick, then placed in a forced-air oven at 60° C. for various periods to determine if they were stable and would function after aging.

The samples were placed one at a time in a stainless steel boat within a 1 inch o.d. stainless steel tube. Hydrogen was passed over the samples at a flow rate of 6-1/min. A phase-controlled temperature regulator and programmer controlled the temperature in the boat and the temperature in the boat was measured by mounting a hot junction chromel-alumel thermocouple within a small hole in the boat. The output of the thermocouple and the detector were monitored on a two-pen potentiostatic recorder. At 60° C./min. heating rate was maintained in each experiment after the insertion of the sample in the boat. The "alarm" temperature at which considerable thermoparticulation occurred was taken from the chart; this corresponded to a 50% decrease in the initial ion current of the Generator Condition Monitor (usually 0.8 to 0.4 mA).

The following table gives the compounds tested, the diameter of the largest decomposition product formed, the temperature at which the vapor pressure of the decomposition products is 10 mm, and the actual thermoparticulating temperature.

The Fatty Acid Family and Their Approximate Molecular Dimensions

| Name | Formula | "Diameter" of Molecule*, Å | Temp. at which Vapor Pres. = 10 mm (°C.)** | Thermoparticulating Temp. (°C.) |
|---|---|---|---|---|
| Caprylic Acid | $C_8H_{16}O_2$ | 20 | | |
| Nonanoic Acid | $C_9H_{18}O_2$ | 22 | | |
| Decanoic Acid | $C_{10}H_{20}O_2$ | 25 | | |
| Hendecanoic Acid | $C_{11}H_{22}O_2$ | 28 | 149 | 156 |
| Lauric Acid | $C_{12}H_{24}O_2$ | 30 | 166 | 168 |
| Tridecanoic Acid | $C_{13}H_{26}O_2$ | 33 | 181 | 184 |
| Myristic Acid | $C_{14}H_{28}O_2$ | 35 | 190 | 191 |
| Pentadecanoic Acid | $C_{15}H_{30}O_2$ | 38 | | |
| Palmitic Acid | $C_{16}H_{32}O_2$ | | 206 | 210 |
| Stearic Acid | $C_{18}H_{36}O_2$ | | 225 | 229 |

*A. I. Kitaigorodskii, "Organic Chemical Crystallography", Consultants Bureau Publishers, New York, 1961.
**Handbook of Chemistry and Physics, 49th Edition, The Chemical Rubber Co., Cleveland, Ohio, 1968, Section D120 to D135.

As the above table shows, no signals were obtained for caprylic acid, nonanoic acid, or decanoic acid indicating that the diameter of the decomposition products must be greater than 25Å. It was also discovered that there was an excellent correspondence between the temperature at which the vapor pressure of the decomposition products is 10 mm and the actual thermoparticulation temperature.

EXAMPLE 2

Example 1 was repeated using other types of compounds. The following table gives the temperature at which the decomposition products had a vapor pressure of 10 mm, and the actual thermoparticulation temperature.

| | Temperature at 10 mm (°C.) | Thermoparticulation Temperature (°C.) |
|---|---|---|
| Tetracosane | 238 | 232 |
| Cetyl alcohol | 178 | 182 |
| Benzoic anhydride | 198 | 203 |
| Phenanthrene | 173 | 177 |
| Biphenyl | 117 | 121 |
| 2-Naphthoic acid | 203 | 200 |
| 2-Naphthol | 146 | 145 |

EXAMPLE 3

Example 1 was repeated using other types of compounds. The following table gives the compounds tested, their predicted thermoparticulation temperature and the actual thermoparticulation temperature obtained.

| | Thermoparticulation Temperature, °C. | |
|---|---|---|
| Compound | Predicted[1] | Experimental[2] |
| $BF_3$: monoethylamine complex | 100–150 | 140 |
| $BF_3$: dimethyl formamide complex | 100–150 | 105 |
| Glyoxime | 150–200 | 167 |
| Thiosemicarbazide | 150–200 | 175 |
| Cyclohexane Sulfamic Acid | 150–200 | 168 |
| 2,4-Dinitro-1-naphthol | 150–200 | 172 |
| Triethyl, n-propylammonium iodide | 150–200 | 155 |
| Sulfabenzamide | >200 | >200 |
| Sulfadiazine | >200 | >200 |
| Zinc Oxalate | >200 | >200 |
| Zinc Formate | >200 | >200 |
| Zinc Tartrate | >200 | >200 |
| Zinc Laurate | >200 | >200 |
| Zinc Palmitate | >200 | >200 |

[1]From molecular size, vapor pressure, and activation energy data given in: (1) "Handbook of Chemistry and Physics", 49th Edition, The Chemical Rubber Co., 1968; (2) "The Chemist's Companion", A. J. Gordon, Wiley Interscience, 1972; (3) "The Condensed Chemical Dictionary", A. Rose, 7th Edition, Reinhold Co., 1966; (4) "Kinetic Data on Gas Phase Reactions"; S. W. Bensen, Nat. Bur. Stand., 1970.
[2]Using a Generator Condition Monitor.

What we claim is:

1. A room temperature, air dryable coating composition comprising about 20 to about 250 phr of at least one thermoparticulating compound and a solution in an organic solvent of a resinous carrier air-dryable at room temperature which is substantially unreactive with said thermoparticulating compound and which is stable when cured, said thermoparticulating compound being selected from the group consisting of:

oximes having the general formula

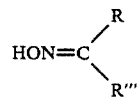

where R''' is R or

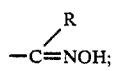

each R is independently selected from the group consisting of hydrogen, alkyl to $C_{20}$, aryl, alkaryl to $C_{20}$, aralkyl to $C_{20}$, heterocyclic including ring nitrogen, oxygen or sulfur, and aryl with nitro or halide substituents.

2. A composition according to claim 1 wherein R''' is

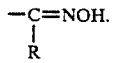

3. A composition according to claim 1 wherein the amount of said thermoparticulating compound is about 40 to about 60 phr and the amount of said solvent is about 45 to about 55% (by weight based on said resinous carrier).

4. A composition according to claim 1 wherein said resinous carrier is an epoxy resin.

5. A composition according to claim 4 which includes about 0.1 to about 3 phr of a drier for said epoxy resin.

6. A composition according to claim 1 wherein the solvent in said solution is toluene.

7. A composition according to claim 1 wherein said thermoparticulating compound is dispersed in said solution.

8. A method of protecting electrical apparatus from damage due to overheating and for thereafter determining the location of said overheating, said apparatus including a gas stream and a monitor for detecting particles in said gas stream and for emitting a signal when said particles are detected comprising:
 (A) preparing a composition according to claim 1;
 (B) applying said composition to said electrical apparatus at positions exposed to said gas stream;
 (C) evaporating said solvent; and
 (D) monitoring said gas stream for the presence of particles therein.

9. A method according to claim 8 including the additional last step of inspecting said apparatus visually for blistered and darkened areas, after particles have been detected in said gas stream, to locate the area of overheating.

10. A method according to claim 8 including the additional last steps of collecting a sample of said particles when they are detected in said gas stream, and analyzing them.

11. A thermoparticulating coating comprising a solid layer of a composition according to claim 1.

12. A coating according to claim 11 which is about 1/16 to about ½ inches thick.

13. A thermal detection system for electrical apparatus cooled by a gas stream comprising a coating according to claim 11 on a portion of said electrical apparatus exposed to said stream and a monitor for detecting the presence of particles in said gas stream.

14. A room temperature, air dryable coating composition comprising about 20 to about 250 phr of at least one thermoparticulating compound and a solution in an organic solvent of a resinous carrier air-dryable at room temperature which is substantially unreactive with said thermoparticulating compound and which is stable when cured, said thermoparticulating compound being selected from the group consisting of:
 triphenyltin chloride-benzyldimethylamine,
 triphenyltin chloride-morpholine,
 triphenyltin chloride-n-propylamine,
 diphenyltin dichloride-morpholine,
 diphenyltin dichloride-benzyldimethylamine,
 tris (ethylenediamine)-chromium (III) chloride,
 pyridine-chromium (III) oxide,
 boron trifluoride-monoethylamine,
 antimony pentafluoride-triethylamine,
 antimony pentachloride-pyridine,
 titanium tetrachloride-morpholine,
 tetrabutyl phosphonium acetate,
 tetrabutyl phosphonium chloride,
 triphenylmethyl phosphonium iodide,
 methyltrioctyl phosphonium dimethyl phosphate,
 tetrabutylarsonium chloride,
 tetraphenylarsonium iodide,
 catechol-antimony pentachloride,
 catechol-antimony pentafluoride,
 tetrabutyl stibonium chloride,
 tetraphenyl stibonium iodide,
 triphenyl methyl stibonium bromide,
 n-butylamine picrate,
 triethylamine picrate,
 m-phenylene diamine picrate,
 1-methylimidazole picrate,
 triethylmethyl ammonium chloride,
 trimethylethyl ammonium iodide,
 benzyl dimethyl ammonium bis (o-phenylene dioxy) phenyl siliconate,
 triethylammonium bis (o-phenylene dioxy) phenyl siliconate,
 triethanolamine bis (o-phenylene dioxy) phenyl siliconate,
 benzyl sulfamic acid,
 napthyl sulfamic acid,
 benzal doxime, and
 benzophenone oxime.

* * * * *